(12) United States Patent
Shah et al.

(10) Patent No.: US 6,399,027 B1
(45) Date of Patent: *Jun. 4, 2002

(54) PERFUME-CONTAINING CAKE, PROCESS FOR MAKING IT, AND ARTICLES USING IT

(75) Inventors: Pravin L. Shah, Wyomissing, PA (US); Merrill Heatter, 1101 N. Roxbury Dr., Beverly Hills, CA (US) 90210

(73) Assignee: Merrill Heatter, Beverly Hills, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/296,696

(22) Filed: Apr. 21, 1999

Related U.S. Application Data

(63) Continuation-in-part of application No. 09/175,798, filed on Oct. 20, 1998.

(51) Int. Cl.⁷ .................................................. A62B 7/08
(52) U.S. Cl. .......................... 422/124; 422/1; 422/121; 422/122; 422/123

(58) Field of Search ............................ 422/1, 121, 122, 422/123, 124

(56) References Cited

U.S. PATENT DOCUMENTS

| 4,500,725 A | * | 2/1985 | Yemoto et al. | 556/482 |
| 4,528,155 A | * | 7/1985 | Elder | 264/174 |
| 4,663,315 A | * | 5/1987 | Hasegawa et al. | 514/86 |
| 4,833,172 A | * | 5/1989 | Schwartz et al. | 521/62 |
| 4,942,973 A | * | 7/1990 | Bowie | 220/201 |
| 4,961,532 A | * | 10/1990 | Tangney | 239/60 |
| 5,460,787 A | * | 10/1995 | Colon | 422/123 |

* cited by examiner

Primary Examiner—Robert J. Warden, Sr.
Assistant Examiner—Imad Soubra
(74) Attorney, Agent, or Firm—Donald D. Mon

(57) ABSTRACT

A perfumed cake and a method for making it. The cake is resistant to higher temperatures such as those produced by hair dryers and can provide perfume for its air stream. The cake is molded from a mixture of two kind of pellets. The first kind of pellet is a mixture of virgin polypropylene, virgin polyethylene or their combinations, and perfumed. The second kind of pellet is a mixture of virgin polypropylene virgin polyethylene or their combinations, and glass fibers. The two kinds of pellets are mixed and molded into a cake.

20 Claims, 1 Drawing Sheet

PERFUME-CONTAINING CAKE, PROCESS FOR MAKING IT, AND ARTICLES USING IT

CROSS-REFERENCE TO PENDING APPLICATION

This is a continuation-in-part of applicant's co-pending U.S. patent application Ser. No. 09/175,798, filed Oct. 20, 1998.

FIELD OF THE INVENTION

A method for making a perfumed cake which is resistant to elevated temperatures, the cake produced by this method, and use of this cake with a stream of high temperature air such as a hair blower to infuse aroma into the stream of air.

BACKGROUND OF THE INVENTION

Fragrances and perfumes are widely used to freshen air by masking an unpleasant odor or by infusing an agreeable odor into it.

Frequently a substance is sprayed into the air, or is extracted from a solid cake by a fluid stream flowing over its surface, either liquid or gas. There are low temperature applications which involve no special problems. Water and alcohol are frequently used in a material to be sprayed. Organic plastic materials such as polyethylene, polypropylene and polyvinyl chloride can be used for a matrix to contain the fragrance in a solid cake. Such matrix materials tolerate and are useful in normal temperatures below those at which their function is degraded.

Fragrances and perfumes are usually oily, and will tolerate elevated temperatures without significant degradation. However, conventional materials for holding them in a solid body will not tolerate substantially elevated temperatures. Instead they will melt or otherwise degrade, and will not provide a body which is suitably shape-retentive, There are numerous applications where a high-temperature airstream can be improved by the infusion of a fragrance or perfume. One example is the conventional hair dryer, especially hand-held hair dryers, in which the airstream temperature is often as high as 200 degrees F. Known plastic cakes with properties amenable to holding and releasing fragrances and perfumes are quickly melted away at higher temperatures. Organic plastic materials that resist higher temperatures are well known, but they do not accept perfumes.

For this reason, perfume exuding attachments to hair dryers, both stationary and hand-held, have not been produced. It is an object of this invention to provide a composite organic plastic body (cake) which can releasably hold perfumes, and can withstand 300 degrees F temperatures to assure flame and smoke resistance, and the 200 degrees F temperature commonly produced by hair dryers.

This will enable, for example, a clip-on device which can readily be attached to the outlet of a hair dryer to impart or infuse perfume into the existing air stream.

It is another object of this invention to provide the body in a shape conducive to smooth air flow over its surface so as to cause least turbulence, while still releasing sufficient perfume from the body.

BRIEF DESCRIPTION OF THE INVENTION

This invention comprehends the combination of a hot air source, for example but not of limitation a hand-held hair dryer, which produces a rapid stream of hot air to dry the hair, together with a body (herein called "cake") in contact with the air stream.

According to this invention, the body incorporates a fragrance or perfume (collectively called "perfume" herein) in a matrix with a surface in contact with the stream, from which the air stream can remove perfume for infusion into the air stream.

According to a preferred feature of this invention, the matrix is able to hold the perfume throughout its mass, to resist flame and smoking at temperatures up to 300 degrees F and to resist melting or plastic deformation at temperatures up to 300 degrees F.

A matrix material suitable for this invention comprises virgin polypropylene or virgin polyethylene or their mixture compounded with short glass fibers to raise its heat deflection temperature to a sufficient value, while still enabling the incorporation of perfume into the polypropylene or polyethylene.

For convenience in disclosure, the virgin polypropylene, virgin polyethylene, or their mixture is referred to herein as "Poly", signifying either one or their mixture in any ratio.

The above and other features of this invention will be fully understood from the following detailed description and the accompany drawings, in which:

DETAILED DESCRIPTION OF THE INVENTION

Figure 1:
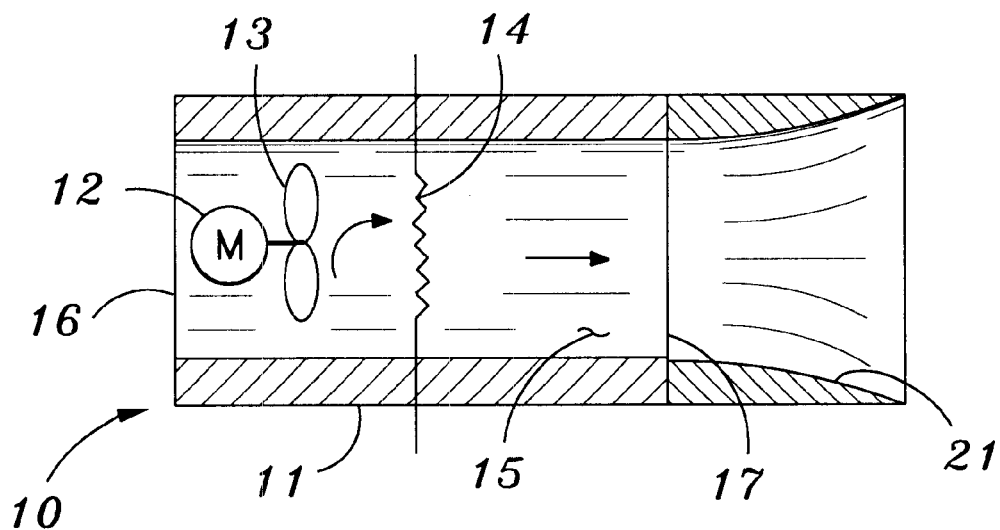
FIG. 1 is an axial cross-section, partly in schematic notation, showing the presently-preferred embodiment of the invention.
Figure 2:
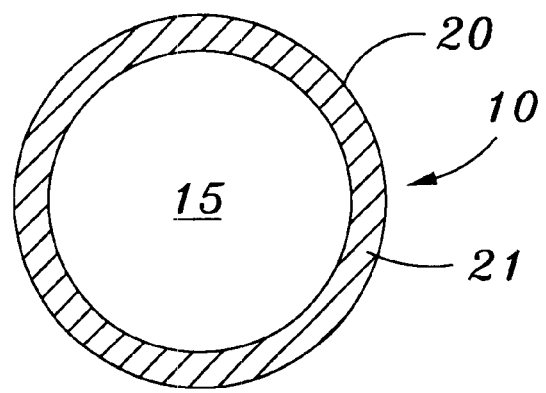
FIG. 2 is a right hand view taken at line 2—2 in FIG. 1.

A source 10, such as a hand-held hot air hair dryer is schematically shown in FIG. 1, because its shape or nature is immaterial to the invention. It has a frame 11 which encloses a motor 12, a fan 13, and a heater coil 14 in an air conduit 15. The conduit has an inlet 16 and an outlet 17. Suitable electrical connections and switches (not shown) are provided to control the speed of the motor and the temperature of the heating coil.

A cake 20 according to this invention is attached to the frame by a clip (not shown) or by any other fastener means, preferably releasable so an exhausted cake can be replaced by a new one. While the cake could if desired be placed directly in the stream, the turbulence and resistance it would cause are undesirable. For this reason it is preferably provided as a ring surrounding the exiting air stream with an internal surface 21 exposed to and in contact with the air stream.

While surface 21 may be of any shape, for example a converging cone, a cylinder, or an expanding cone, best results are attained with an enlarging nozzle shape whose axial cross-section is an expanding curve. This provides a longer travel path of air along the surface enabling a somewhat shorter cake to be utilized.

Prior efforts to utilize organic plastic materials that can resist deformation, flame and smoke, and also usefully contain perfume have failed. For example, polysufones and polystyrenes will resist higher temperatures, but do not sufficiently accept perfume. Polyethylene, which is widely used alone to contain perfume, softens and melts at too low a temperature. In a test, polypropylene with lemon perfume melted away at 200 degrees F.

The inventor herein attempted to reinforce polypropylene with glass fibers to strengthen it and increase its heat resistance. Polypropylene itself has a heat deflection temperature of 190 degrees F. Addition of glass fibers as a compound mix of polypropylene and glass fibers did in fact increase the heat deflection temperature to about 300 degrees F. However, the reinforced material would not accept the perfume. It appears that this fiber somehow "coats" the polypropylene so as to close its pores and produce the gross effect of a glass-like surface instead of a porous polypropylene surface, as seen by the perfume.

The objectives of strengthening with a fiber having a smooth and large area surface, and acceptance of perfume, are clearly opposed to each other. Reduction of either property will result in a useless product. By means of this invention, a cake incorporating polypropylene, glass fibers and perfume has been attained, and it does resist deformation, smoking and flame at the output temperature of a hair dryer, namely about 200 degrees F in the air stream, with flame and smoke resistance to about 300 degrees F.

This is the preferred formulation, and provides best results. However, it has been found that, surprisingly, virgin polyethylene, or its mixtures with virgin polypropylene can, when used in the process disclosed herein, provide a product which while not optimal will provide results that are acceptable for less stringent applications. These therefore fall within the scope of this invention.

The preferred cake is produced using virgin polypropylene with a melt flow rate of 5–15, and suitable molecular weight between about 100,000 and 450,000, preferably about 250,000. Solvay polypropylene grade PP 1900, obtained from Solvay Polymers, 3333 Richmond Avenue, Houston, Tex. 77098 is the presently-preferred polymer.

Glass fibers used in this device preferably have a long length about 1/8"–1/4" inches and a diameter about 10–17 microns inches.

The perfumes themselves may have any desired fragrance, lavender, lemon or jasmine, for example. Oil base perfumes and fragrances are preferred for their acceptance by polypropylene and polyethylene. A useful example is an oil-based perfume sold by Belleaire Fragance, Inc. 1600 Baskin Road, Mundelein, Ill. 60060 under its specification #21841, a lavender perfume.

The above components have previously been said to be incompatible for purposes of this invention. However the inventor herein has overcome the problems by providing a specific method to prepare it, thereby producing a cake and combination of cake and hot air source which has heretofore been unattainable.

As a first step, oil based perfume is mixed the poly, preferably with virgin polypropylene, in a mixer. The mixture is preferably a twin screw extruder that utilizes low shear mixing at an elevated temperature, usually between about 380 degrees to 420 degrees F. The resulting mix is extruded as a strand, cut into pellets, cooled to room temperature, and may then be stored. This is called "perfume plastic concentrate" ("PCC"). The presently preferred PCC is 10 pounds of resin and 2.5 pounds of perfume.

As a separate step, virgin polypropylene and glass fibers are compounded together for form a "plastic-glass concentrate" ("PPG"). This step may also utilize a twin screw extruder operating at a temperature between about 380 degrees and 420 degrees F. These fibers are mixed into the polypropylene, and the mix is extruded, cut into pellets, cooled and stored if desired. It will be noted that this PPG mix is incapable of suitably accepting perfume.

The weight percentage of fiber glass to plastic should be about 30%. A percent less than about 20% will not reliably produce a suitable product, while percentages much above about 35% do not provide significant improvement.

As a third and final step, appropriate amounts of PPC and PPG are tumbled together to form a properly proportioned mix for injection. Then this mix is fed to an injection molding machine heated to about 350 degrees–375 degrees F., at which temperature this mix is injection molded into a desired shape, removed from the mold and cooled. It is then ready for use. A 30 second mold cycle has been found to be appropriate for the nozzle shape shown in FIG. 1. It has an outer diameter of about 2.6 inches, an internal diameter of about 2" at its smaller end and about 2.55" at its larger end.

A mix of one pound of PPC and four pounds of PPG appears to be about right for intensity of aroma, containing about 5% by weight of active perfume. A mix of two pounds of PPC and three pounds of PPG is too strong with about 10% active perfume. A much lower concentrate of active perfume does not seem to be strong enough. Minor experimentation with regard to fragrance strength will soon disclose the most appropriate level.

A less suitable, but still functional product may be produced by the same process and conditions with the use of virgin polyethylene. Whenever virgin polypropylene is given as an example herein, virgin polyethylene or mixtures of the two may be substituted instead. The molecular weights and other parameters are suitably alike. However, as a specific example of the use of polyethylene, Don Chemical Corporation's low density polyethylene grade 4012M is substituted for the polypropylene in the above preferred example. This polyethylene has a molecular weight of about 100,000 and melt flow rate of about 10–15. While the heat deflection temperature was only about 207 degrees F, the product did retain perfume for up to four hours of continuous usage, which is sufficient for many purposes.

The term "molecular weight" (MW) as used in the preceding paragraph is the sum of the atomic weights of the elements that comprise the formulations MW is a dimensionless number in which the atomic weight of each element, for formulation proposes, is a dimensionless number on the scale in which atomic oxygen has the weight of 16,000 g/mole.

The term "melt flow" rate is a standard read-out of an established test used throughout the polymer industry. It is based on a Standard defined by ASTM (the American Society for Testing Materials). In this case relation is made to its published Standard Test Method D 1238. The units are grams/10 minutes.

The following quotation is from "Melt Rheology" by Dr. Dealy, published 1990, by Van Nostrand, page 327:

"Standard Test Method D1238 is based on a a specific embodiment of this concept. This standard method prescribes the exact geometry of the barrel and die and a choice of several standard temperatures and driving weights for various materials. Condition "E" is the one most used with polyethylene and involves a test temperature of 190 degrees C and a total load of 2.16 kg. The Standard procedure involves the measurement of the mass of polymer that is extruded in 10 minutes. The "flow rate", expressed as grams/10 minutes (or dg/min) is the number reported. When condition E is used, this quantity is commonly called the "melt index" or MI. Obviously, the MI value increases as the viscosity decreases, i.e., a "high MI" resin has a low viscosity."

The product produced by the above process has a sensibly long useful life, and is of a size and shape to be easily and attractively packaged. It provides the advantages of plastic's acceptance of perfumes, and the strengthening of glass fibers for temperature resistance.

This invention is not to be limited by the embodiments shown in the drawings and described in the description, which are given by way of example and not of limitation, but only in accordance with the scope of the appended claims.

We claim:

1. A solid, composite molded perfume-containing cake to exude perfume into a flowing hot airstream comprising:

first pellets which consist essentially of virgin polypropylene of virgin polyethylene, or their combinations, mixed with perfume; and second pellets which consist essentially of virgin polypropylene or virgin polyethylene, or their combinations mixed intimately with glass fibers;

a uniformly-distributed composite of said first and second pellets having been molded under heat to form said cake, said cake thereafter having been cooled, and having an exposed surface resistant to heat deformation at temperatures up to about 300 degrees F, and having the property of releasing said perfume into a flowing hot stream of air which passes over a portion of said surface.

2. A cake according to claim 1 in which the Poly has a melt flow rate between about 5 and 15, a molecular weight between about 100,000 and about 450,000, and in which the glass fibers have a length between about ⅛ and ¼ inches and a diameter between about 10 and 17 microns.

3. A cake according to claim 2 in which said molecular weight is about 250,000, and the melt flow rate is about 10.

4. A cake according to claim 1 shaped as a ring-like body, said portion being located inside said ring-like body for being contacted by a stream of heated air.

5. A cake according to claim 4 in which said portion is a nozzle shape having in increasing diameter from one end to its other end.

6. In combination:

a source of a stream of heated air, said source having a frame; and a cake according to claim 1 attached to said frame in a location to be contacted by said stream of air to infuse perfume into said stream.

7. A combination according to claim 6 in which the poly has a melt flow rate between about 5 and 15, a molecular weight between about 100,000 and about 450,000, and in which the glass fibers have a length between about ⅛ and ¼ inches and a diameter between about 10 and 17 microns.

8. A combination according to claim 7 in which said molecular weight is about 250,000, and the melt flow rate is about 10.

9. A combination according to claim 6 in which said stream exits from said frame, said cake being formed as a ring-like body passing said stream, and having an internal surface surrounding and in contact with said stream to exude perfume from said cake into the stream.

10. A combination according to claim 9 in which said internal surface is a nozzle shape having an increasing diameter in the direction of stream flow.

11. A combination according to claim 9 in which the polypropylene has a melt flow rate between about 5 and 15, a molecular weight between about 100,000 and about 450,000, and in which the glass fibers have a length between about ⅛ and ¼ inches and a diameter between about 10 and 17 microns.

12. A combination according to claim 6 in which said Poly consists essentially of polypropylene.

13. A cake according to claim 1 in which said Poly consists essentially of polypropylene.

14. A cake according to claim 13 in which the polypropylene has a melt flow rate between about 5 and 15, a molecular weight between about 100,000 and about 450,000, and in which the glass fibers have a length between about ⅛ and ¼ inches and a diameter between about 10 and 17 microns.

15. The method of making solid composite molded perfume-containing predominantly plastic cake receptive to heat deformation at temperatures of up to about 300 degrees F, said method comprising:

forming first pellets which consist essentially of virgin polypropylene, virgin polyethylene, or their combinations, mixed with perfume;

separately forming second pellets which consist essentially of virgin polypropylene, virgin polyethylene, or their combination, mixed intimately with glass fibers; and uniformly mixing said first and second pellets together as an intimate composite and molding the resulting composite of pellets under conditions of elevated temperature in a mold, and cooling the resulting cake.

16. The method according to claim 15 in which the poly has a melt flow rate between about 5 and 15, a molecular weight between about 100,000 and about 450,000, and in which the glass fibers have a length between about ⅛ and ¼ inches and a diameter between about 10 and 17 microns.

17. The method according to claim 16 in which said molecular weight is about 250,000, and the melt flow rate is about 10.

18. A method according to claim 15 in which said Poly consists essentially of polypropylene.

19. A method according to claim 18 in which said polypropylene has a melt flow rate between about 5 and 15, a molecular weight between about 100,000 and about 450,000, and in which the glass fibers have a length between about ⅛ and ¼ inches and a diameter between about 10 and 18 microns.

20. A combination according to claim 19 in which said stream exits from said frame, said cake being formed as a ring-like body passing said stream, and having an internal surface surrounding and in contact with said stream to exude perfume from said cake into the stream.

* * * * *